US010012616B2

(12) United States Patent
Aura et al.

(10) Patent No.: US 10,012,616 B2
(45) Date of Patent: Jul. 3, 2018

(54) ACOUSTIC EMISSION SYSTEM AND METHOD FOR PREDICTING EXPLOSIONS IN DISSOLVING TANK

(71) Applicant: Andritz Inc., Glens Falls, NY (US)

(72) Inventors: Kari Aatos Aura, Tampere (FI); Alvaro Moura Timotheo, Alpharetta, GA (US)

(73) Assignee: Andritz Inc., Glen Falls, NY (US)

( * ) Notice: Subject to any disclaimer, the term of this patent is extended or adjusted under 35 U.S.C. 154(b) by 136 days.

(21) Appl. No.: 15/333,695

(22) Filed: Oct. 25, 2016

(65) Prior Publication Data

US 2017/0131240 A1    May 11, 2017

Related U.S. Application Data

(60) Provisional application No. 62/252,221, filed on Nov. 6, 2015.

(51) Int. Cl.
| | |
|---|---|
| *D21G 9/00* | (2006.01) |
| *D21C 11/12* | (2006.01) |
| *D21C 11/10* | (2006.01) |
| *G01N 29/44* | (2006.01) |
| *G01N 29/02* | (2006.01) |

(52) U.S. Cl.
CPC ............ *G01N 29/02* (2013.01); *D21C 11/10* (2013.01); *D21C 11/12* (2013.01); *D21C 11/122* (2013.01); *D21G 9/0009* (2013.01); *G01N 29/4481* (2013.01)

(58) Field of Classification Search
CPC .... G01N 29/02; G01N 29/4481; D21C 11/12; D21C 11/10; D21C 11/122

USPC ............................................... 73/587
See application file for complete search history.

(56) References Cited

U.S. PATENT DOCUMENTS

| 4,462,319 A | 7/1984 | Larsen | |
|---|---|---|---|
| 4,960,079 A * | 10/1990 | Marziale | F22B 37/421 122/504.2 |
| 5,101,774 A | 4/1992 | Marziale et al. | |
| 5,817,927 A * | 10/1998 | Chen | G01M 3/228 73/40.7 |

(Continued)

FOREIGN PATENT DOCUMENTS

| WO | 97/24742 | 7/1997 |
|---|---|---|
| WO | 2008028991 | 3/2008 |

OTHER PUBLICATIONS

Tran, Honghi, et. al. "Passive Acoustic Monitoring of Recovery Boiler Dissolving Tank Operation", Proceedings of the Canadian Society for Mechanical Engineering International Congress 2014, CSME International Congress 2014, Jun. 1-4, 2014, Toronto, Ontario, Canada.

(Continued)

*Primary Examiner* — J M Saint Surin
(74) *Attorney, Agent, or Firm* — Kerri Hochgesang; Robert Joseph Hornung

(57) ABSTRACT

The present disclosure describes a system for predicting explosions in a dissolving tank. The system includes acoustic emission sensors placed in or around the dissolving tank. By filtering the recorded frequencies to the range which is most sensitive for desired explosions "fingerprints," it is possible to predict a smelt influx before the smelt influx occurs as well as program response actions to prevent compromising explosions.

32 Claims, 5 Drawing Sheets

(56) References Cited

U.S. PATENT DOCUMENTS

| | | | |
|---|---|---|---|
| 5,847,266 A * | 12/1998 | Nevruz | F22B 37/421 |
| | | | 73/40.5 R |
| 5,852,793 A | 12/1998 | Board et al. | |
| 5,976,319 A | 11/1999 | Paju et al. | |
| 6,351,713 B1 | 2/2002 | Board et al. | |
| 6,679,119 B2 | 1/2004 | Board | |
| 6,684,700 B1 | 2/2004 | Board | |
| 7,505,852 B2 | 3/2009 | Board | |
| 7,806,127 B2 * | 10/2010 | Gibowski | F23G 7/04 |
| | | | 134/104.1 |
| 9,206,548 B2 | 12/2015 | Kujanpaa | |
| 9,759,610 B2 * | 9/2017 | Maity | G01J 5/0014 |
| 2011/0088471 A1 * | 4/2011 | Fitzpatrick | G01N 29/036 |
| | | | 73/579 |

OTHER PUBLICATIONS

Ponsaud, Philippe, Extended European Search Report, dated Jan. 30, 2017, pp. 1-5, European Patent Office, Munich, Germany.

Yamasaki, Hiroshi, et. al., Application of Acoustic Emission Measurement for Secondary Atomization Processes of a Burning Emulsion Droplet, Journal of the Japan Institute of Energy, 2014, 127-134, vol. 93 Issue No. 2, Japan.

* cited by examiner

ACOUSTIC EMISSION SYSTEM AND METHOD FOR PREDICTING EXPLOSIONS IN DISSOLVING TANK

CROSS-RELATED APPLICATION

This application claims the benefit of U.S. Provisional Pat. App. No. 62/252,221 filed on Nov. 6, 2015, the entirety of which in incorporated herein by reference.

BACKGROUND OF THE INVENTION

1. Technical Field

The present disclosure relates generally to chemical pulping and particularly to recovery boilers and dissolving tanks used in the pulp and paper industry.

2. Related Art

Chemical pulping converts lignocellulosic biomass to pulp fibers of various lengths. In the pulp and paper industry, the lignocellulosic biomass often comprises wood chips; but lignocellulosic material may include other plant-based biomass in which the protein lignin is closely associated with cellulosic sugar molecules. With processing, operators can isolate cellulosic pulp fibers for use in a variety of commercial applications, including paper manufacturing.

When wood is the primary lignocellulosic material for example, production may begin with a log. A debarker removes the bark from (or "debarks") logs, and a chipper comminutes the logs into small chips. Depending on the particular process and application, operators may pretreat these chips with steam and chemicals to expand pores in the lignocellulosic biomass, or operators may send dried chips directly into a chemical digester. Continuous chemical digesters are generally cylindrical and may be several stories high.

In the digester, operators typically introduce white liquor and steam into the digester's upper section. In the Kraft process, the "white liquor" often consists of a sodium hydroxide and sodium sulfide solution. Over the course of several hours, the steamed biomass moves through the digester as white liquor dissolves the lignin. Lignin is a protein that binds the cellulose and hemicellulose in the biomass together. Removal of lignin permits operators to isolate fibers comprising mainly cellulose and hemicellulose. As the lignin and other ancillary biomass compounds dissolve into the liquor, the liquor darkens and becomes "black liquor".

After the black liquor solution exits the digester, equipment isolates the cellulosic pulp fibers from the remaining black liquor. Whereas white liquor contains sodium hydroxide and sodium sulfide, the black liquor contains sodium carbonate and sodium sulfate respectively. Sodium carbonate and sodium sulfate are the products of the white liquor's chemical reaction with the lignin and other compounds in the digester. The products, sodium carbonate and sodium sulfate, are generally less useful for digesting lignin.

While sodium hydroxide and sodium sulfide are generally inexpensive chemicals, purchasing new solutions of sodium hydroxide and sodium sulfide for every new batch of lignocellulosic biomass is generally cost prohibitive. For this reason, many chemical pulp mills use pyrolytic chemical recovery systems to convert at least a portion of the sodium carbonate and sodium sulfate back into useful sodium hydroxide and sodium sulfide.

New black liquor from a chemical digester is generally dilute and non-combustible. Therefore, to prepare black liquor for pyrolysis, operators generally funnel the black liquor through flash tanks or other evaporation steps to increase the amount of solid particles concentrated in the black liquor. Operators then heat the concentrated black liquor before injecting the concentrated black liquor through spray nozzles into a chemical recovery boiler. The spray nozzles create coarse droplets. The recovery boiler evaporates the remaining water from the droplets and the solid compounds in the black liquor undergo partial pyrolysis. The inorganic compounds that remain fall to the bottom the furnace and accumulate in a char bed. Some of the carbon and carbon monoxide in the char bed can act as catalysts to convert sodium sulfate into sodium sulfide, which can then be collected from flue gas near the top of the furnace.

The remaining inorganic compounds in the char bed eventually melt and flow as a smelt through one or more smelt spouts at the bottom of the recovery boiler. Coolant, usually water, may cool the smelt spouts. Coolant tubes may either be integrated into the spout itself, or an ancillary cooling system. The ancillary cooling system is often called a "water jacket" and may surround the outside of the spout. The smelt flowing from the spout falls into a dissolving tank and contacts water or weak white liquor to produce soda lye. The resulting soda lye solution is commonly known as "green liquor."

In a sulfate chemical process, such as the Kraft process, the main component of the green liquor is typically sodium sulfide and sodium carbonate. However, different chemical processes produce green liquor with different inorganic compounds. Operators typically collect the green liquor and transport the green liquor to a causticizing plant to further isolate and concentrate the sodium sulfide and sodium carbonate and thereby reproduce white liquor.

As the smelt contacts the green liquor in the dissolving tank, the smelt explodes and emits a series of audible noises. This is generally known as "banging" by those in the industry. The smelt flowing from the spout is typically between 750 degrees Celsius (° C.) to 820° C., while the average temperature of the green liquor is about 70° C. to 100° C. Moreover, the smelt generally contains reactive alkali metals such as sodium, which reacts explosively with water. Without being bounded by theory, the large temperature differential may increase the reactivity of the smelt and green liquor and thereby cause or contribute to banging. If left unregulated, a sudden influx of smelt may blow up the dissolving tank and recovery boiler, which poses grave risks to nearby operating personnel.

To manage banging, conventional dissolving tanks generally disrupt the smelt as the smelt falls from the spout. Disruptors may be one or more shatter jets, which blast the falling smelt with steam or other fluid at high pressure to create smelt droplets. These droplets have a smaller volume than the overall flow of smelt and therefore, the explosions are generally less intense than they would be if the smelt contacted the green liquor as a continuous, uninterrupted, undisrupted flow. Typically, the end of the smelt spout is elevated above the level of green liquor and these shatter jets disrupt falling smelt as the smelt falls from the spout end.

Occasionally, smelt may cool prematurely in the recovery boiler or spout and decrease or eliminate the smelt flow rate. In this antediluvian state, liquid smelt tends to accumulate behind the obstruction. If the obstruction becomes dislodged, the sudden smelt influx may overwhelm the shatter jet's ability to disrupt the smelt into sufficiently small droplets. Moreover, if the deluge is particularly substantial, the smelt may flow over the sides of the spout and bypass the shatter jets entirely. In other scenarios, a shatter jet may fail. In these situations, the increased volume of smelt contacting the green liquor drastically increases the banging's explosive intensity and risk of explosion.

In many mills, operators commonly move in and amongst the processing equipment to monitor process conditions and output. An explosion in the dissolving tank or recovery boiler poses a serious safety risk to personnel in the immediate vicinity, and the resulting fire poses a serious risk to personnel in the rest of the mill. Such explosions also cause an unregulated amount of pollutants to enter the air and groundwater and predicate significant production loss. Explosions of this scale can inactivate a mill for weeks to months.

SUMMARY OF THE INVENTION

Applicant conceived a system in which acoustic emission sensors are placed in or around the dissolving tank. Applicant has discovered that the acoustic emissions filtered to a programmed frequency range of greater than 20 KHz tend to exhibit a distinctive pattern or "pre-influx fingerprint" closely before a smelt influx occurs. By isolating the recorded frequencies of acoustic emissions to detect a pre-influx fingerprint, it is possible to predict a smelt influx before the smelt influx occurs. Upon detection of a pre-influx fingerprint, an exemplary system disclosed herein may modify a process condition or contain the smelt influx and thereby prevent or mitigate upset conditions, which can contribute to compromising explosions. In other exemplary embodiments, operators may program a smelt control mechanism such as the disruptors or the restrictor plate disclosed in U.S. Pat. No. 9,206,548 to control smelt flow. Measuring acoustic emission events from smelt banging in a dissolving tank may be further used to regulate conditions inside the recovery boiler to thereby control the amount of smelt entering the dissolving tank.

A smelt influx detected by one of more acoustic emission sensors disposed near the disruptor and smelt spout can be corroborated by a "pre-influx fingerprint" comprising an increased rate of acoustic emissions having amplitudes substantially exceeding a first set of processed waveforms by more than 200% and having a frequency of greater than 20 KHz. The acoustic emission system may further comprise a response configured to adjust smelt flow when the acoustic emission system detects a pre-influx fingerprint. The response may comprise restricting smelt flow, changing process conditions within the recovery boiler, or a combination thereof.

The problem of boiler explosions is mitigated by using exemplary embodiments of the system and method disclosed herein. In an exemplary embodiment, the acoustic emission system may comprise acoustic emission sensors configured to detect acoustic emissions. An acoustic emission sensor may comprise a transducer having a resonant frequency, wherein the transducer is configured to convert an acoustic wave into an electric signal. A preamplifier may communicate with the transducer. The pre-amplifier is typically configured to amplify an electric signal. The pre-amplifier generates an amplified signal in turn, and transfers the amplified signal to a data processor. The data processor can be configured to filter the amplified signal to a programmed frequency range above 20 KHz. The data processor may further evaluate frequencies in the programmed frequency range to detect the pre-influx fingerprint. Once the data processor detects the pre-influx fingerprint, the data processor may initiate a response, which may include changing one or more operating conditions in the recovery boiler or activating safety devices to reduce or prevent the smelt influx from contacting the green liquor in the dissolving tank.

In an exemplary system, multiple acoustic emission sensors may be disposed in and around the dissolving tank. For example, acoustic emission sensors comprising a wave guide may be disposed in the wall of the dissolving tank. The acoustic sensor may have a reading end at the end of the wave guide and a second end, opposite the reading end, disposed outside of the dissolving tank. The reading end may be disposed within the dissolving tank. In certain exemplary embodiments, two or more acoustic emission sensors may have wave guides extending into the green liquor. In other exemplary embodiments, an acoustic emission sensor may have a wave guide disposed within the fluid emitted from the disruptor. In still other exemplary embodiments, an acoustic emission sensor may have a wave guide disposed within the dissolving tank above the green liquor level and outside of the disruptor fluid. In other exemplary embodiments, an acoustic emission sensor may be disposed adjacent to the dissolving tank.

Under normal operating conditions the disruptors disperse the smelt flowing off of the smelt spout into smelt droplets. The smelt droplets then contact the green liquor and emit a small "bang." The "bang" comprises both audible acoustic emissions and as acoustic emissions above and below the range of human hearing. Under these normal operating conditions, hundreds of small bangs may occur every second. In an exemplary embodiment of the process, the acoustic emission sensor detects the acoustic emissions and transduces the acoustic emission waves into an electric analog signal. The signal may proceed to a series of pre-amplification stages followed by one or more high pass, low pass or bandpass filter stages to isolate desirable frequencies in a frequency range above 20 KHz. The signal may be further refined before being converted into a digital signal. An analog-to-digital ("A/D") converter may convert the analog signal to a digital signal. The digital signal may then be sent to a data processor such as a field-programmable gate array ("FPGA"), which may utilize either the continuous count method or conduct Fourier Transformation to process and thereby simplify the digital signal. The Fourier Transform may be a Fast Fourier Transform ("FFT"), or other Fourier Transform. In other exemplary embodiments, the FPGA may utilize other signal processing or transformation methods to show maximum correlations on each individual process part e.g. by using the root mean square ("RMS") method, standard deviation method, skewness method, kurtosis method, mean method, variance method, or by utilizing fuzzy logic, neural networks, and other signal processing methods. In still other exemplary embodiments, the data processor may be an application-specific integrated circuit ("ASIC"). Furthermore, an exemplary system may analyze signals produced by the multiple acoustic emission sensors.

An exemplary system may continuously monitor the dissolving tank for smelt influx above a baseline level of smelt flow.

An exemplary system may process and analyze the signals derived from acoustic emissions in the dissolving tank to predict a smelt influx and initiate a response to prevent smelt influx.

A further exemplary system may regulate the operating conditions in the recovery boiler based upon signals derived from acoustic emissions in the dissolving tank.

Yet another exemplary system and method may comprise a computer-based system having software configured to monitor the dissolving tank based on signal input from the acoustic emission sensors. The computer-based system may have defined condition alerts to indicate when a signal exceeds a predetermined signal amplitude threshold.

The problem of upset conditions in dissolving tanks is solved by using a method of monitoring the dissolving tanks comprising: inserting one or more acoustic emission sensors through a wall or roof in the dissolving tank; continuously listening to the amount and intensity ("aggressivity") of banging in the dissolving tank, relaying this banging to a computer system, analyzing the data, comparing with dissolving tank process status and returning an output once the data meets programmed conditions.

A characteristic feature of the arrangement according to an embodiment of the present disclosure is that the present disclosure comprises: a sensor for measuring the acoustic emission caused by the smelt contacting the green liquor. The sensor may comprise a wave guide having a first end and a second end, wherein the first end is disposed at a distance inside the dissolving tank and the second end is located outside of the dissolving tank. The second end may be provided with a piezoelectric sensor configured to convert a received acoustic emission into an analog electric signal. The wave guide may comprise an uninsulated portion for receiving the acoustic emission and an insulated portion disposed downstream of the uninsulated portion. The acoustic emission sensor may further comprise pre-processors for processing the received analog electric signal.

An exemplary method according to the present disclosure comprises: receiving acoustic emission caused by the chemical and thermal reactions of smelt and green liquor in an interior of a dissolving tank through an acoustic emission sensor extending into the interior of the dissolving tank. The method may further comprise converting the acoustic emission into a digital signal, transmitting the digital signal to a computer, and graphing the digital signal on a frequency spectrum to create a graph frequency spectrum. One may then compare the graphed frequency spectrum to a stored frequency spectrum indicative of a normal operating condition, and generate a response when the graphed frequency spectrum exceeds the stored frequency spectrum by more than 200%.

In another exemplary embodiment, the computer may produce a digital output signal that deploys a restrictor plate such as the one described in U.S. Pat. No. 9,206,548.

BRIEF DESCRIPTION OF THE DRAWINGS

The foregoing will be apparent from the following more particular description of exemplary embodiments of the disclosure, as illustrated in the accompanying drawings in which like reference characters refer to the same parts throughout the different views. The drawings are not necessarily to scale, with emphasis instead being placed upon illustrating the disclosed embodiments.

DETAILED DESCRIPTION OF THE INVENTION

Figure 1:
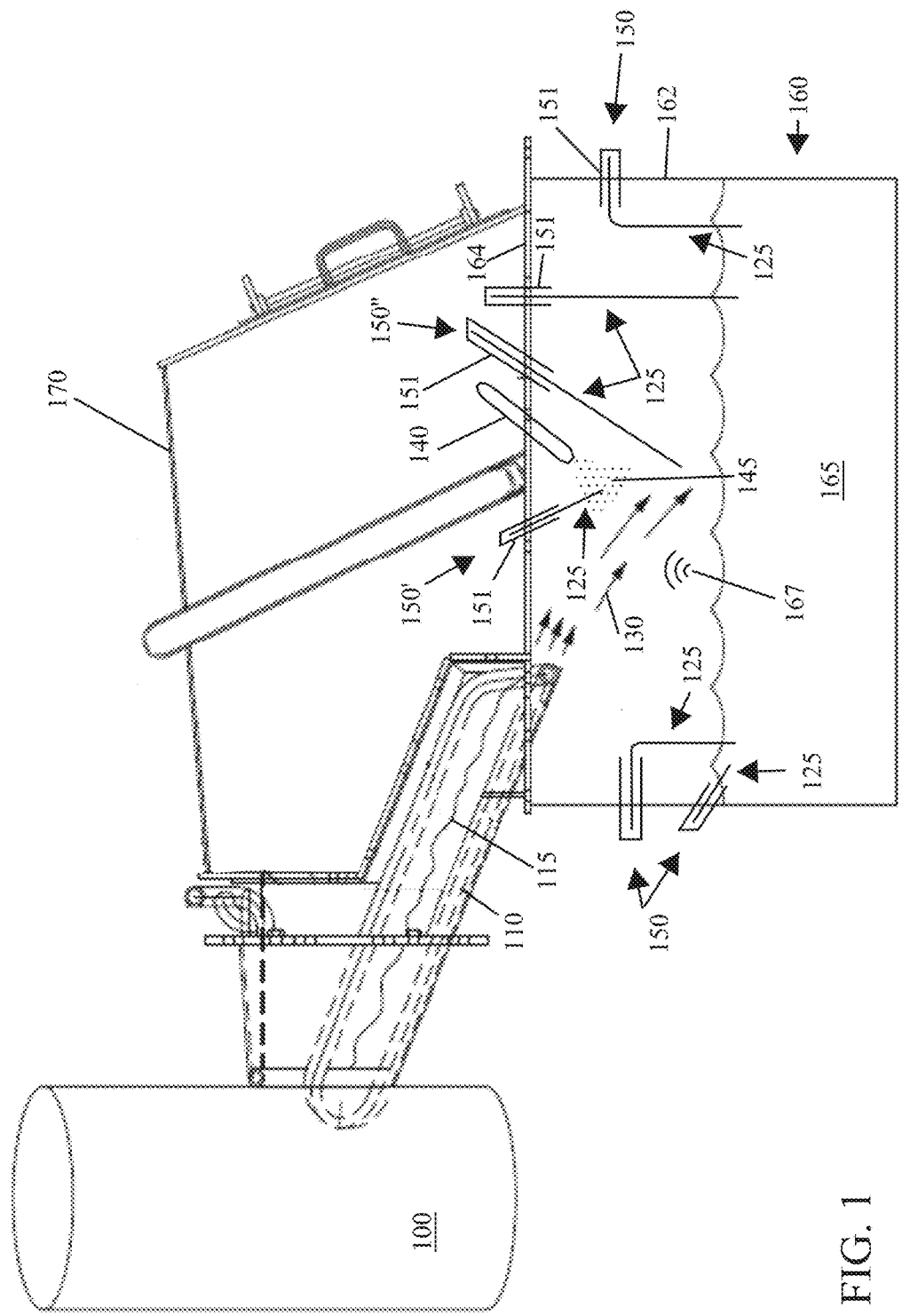
FIG. 1 is a cross sectional side view multiple acoustic emission sensors disposed around a dissolving tank.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Corresponding reference characters indicate corresponding parts throughout the several views. Although the drawings represent embodiments of various features and components according to the present disclosure, the drawings are not necessarily to scale and certain features may be exaggerated in order to better illustrate embodiments of the present disclosure, and such exemplifications are not to be construed as limiting the scope of the present disclosure in any manner.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Although specific terms are used in the following description for the sake of clarity, these terms are intended to refer only to the particular structure of the embodiment selected for illustration in the drawings, and are not intended to define or limit the scope of the disclosure.

The singular forms "a," "an," and "the" include plural referents unless the context clearly dictates otherwise. Numerical values should be understood to include numerical values which are the same when reduced to the same number of significant figures and numerical values which differ from the states value by less than the experimental error of conventional measurement technique of the type described in the present application to determine the value.

All ranges disclosed herein are inclusive of the recited endpoint and are independently combinable (for example, the range "40 decibels ('dB') to 60 dB" is inclusive of the endpoints, 40 dB and 60 dB, and all intermediate values.

As used herein, approximating language may be applied to modify any quantitative representation that may vary without resulting in a change in the basic function to which it is related. Accordingly, a value modified by a term or terms, such as "about" and "substantially," may not be limited to the precise values specified. The modifier "about" should also be considered as disclosing the range defined by the absolute values of the two endpoints. For example the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows or a signal moves through various components, i.e. the signal encounters an upstream component prior to encountering the downstream component.

The terms "top" and "bottom" or "base" are used to refer to locations/surfaces where the top is always higher than the bottom/base relative to an absolute reference, i.e. the surface of the Earth. The terms "upwards" and "downwards" are also relative to an absolute reference; an upwards flow is always against the gravity of the Earth.

FIG. 1 is a schematic diagram depicting a dissolving tank 160 having acoustic emission sensors 150 extending through walls 162 and a top 164 of the dissolving tank 160. Although FIG. 1 depicts a single smelt spout 110 and a single dissolving tank 160, it will be understood that multiple smelt spouts 110 and dissolving tanks 160 may extend around the recovery boiler 100. The acoustic emission sensor 150 has a reading end (222, FIG. 2) and a second end (224, FIG. 2), opposite the reading end 222 disposed outside of the dissolving tank 160. The reading end 222 is disposed within the dissolving tank 160. In other exemplary embodiments, an acoustic emission sensor 150 may be disposed entirely within the dissolving tank 160 such that both the reading end 222 and the second end 224 are disposed within the dissolving tank 160.

In still other exemplary embodiments, an acoustic emission sensor 150 may be disposed entirely outside of the dissolving tank 160 such that both the reading end 222 and the second end 224 are disposed outside of the dissolving tank 160. FIG. 1 depicts multiple acoustic emission sensors 150 disposed through the dissolving tank 160. Multiple acoustic emission sensors 150 can be used to provide additional detailed signal data. An acoustic emission sensor 150 may be glued, fastened, or otherwise attached to the top 164 or walls 162 of the dissolving tank 160. In other exemplary embodiments, an acoustic emission sensor 150 may be engaged to pipes proximate to or communicating with the dissolving tank 160. In still other exemplary embodiments, magnets may engage the acoustic emission sensors 150 to the dissolving tank 160 or to pipes.

As the smelt droplets 130 contact the green liquor 165, the smelt droplets 130 emit acoustic emissions 167. A passerby may hear some of these acoustic emissions 167 as an audible bang. An example acoustic emission sensor 150 may detect the acoustic emissions 167, transduce the acoustic emissions 167 into an electric analog signal 307 (FIG. 3), and pre-amplify the signal 307 before transmitting the amplified signal 311 for further processing. The acoustic emissions 167 may be sound waves or other energetic waves transmitted through the dissolving tank 160.

The acoustic emission sensors 150 may comprise a piezoelectric sensor, a micro-electro-mechanical system ("MEMS") sensor, or other acoustic sensors configured to detect acoustic emissions 167 and transduce the acoustic emissions 167 into an electric signal 307. Furthermore, an acoustic emission sensor 150 may comprise a filter 316 (FIG. 3) such as a broad band acoustic emission filter. In other exemplary embodiments, an acoustic emission sensor 150 may comprise a narrow band acoustic emission filter.

As shown in FIG. 1, a first end of the smelt spout 110 may be disposed in, engaged to, or extend toward the recovery boiler 100 and the second end of the smelt spout 110, opposite the first end of the smelt spout 110 can be, disposed over, engaged to, or extend toward a dissolving tank 160. Smelt 115 from a recovery boiler 100 flows down a smelt spout 110 into the dissolving tank 160. The dissolving tank 160 is generally disposed under a hood 170. Disruptors 140 emit fluid 145 that disrupts the flow of smelt 115 to create smelt droplets 130. The fluid 145 is generally steam. The disruptors 140 may be shatter jet nozzles.

In the depicted embodiment, an acoustic emission sensor 150' extends into the fluid 145 emitted by the disruptor 140. The area in which the fluid 145 extends may be known as the fluid path of the disruptor 140. A wave guide 125 of at least one of the acoustic emission sensors 150 desirably extends into the liquid in the dissolving tank 160. In exemplary embodiments depicted in FIG. 1, the liquid is green liquor 165, but it will be understood that the liquid may be any liquid used in dissolving tanks 160. A wave guide 125 of at least one other acoustic emission sensor 150' does not contact the green liquor 165.

Acoustic emission sensor 150" is configured to detect the first signs of uneven smelt flow. This is an example of using the acoustic emission sensors 150, 150' and 150" in a master-slave processing configuration, wherein a master sensor (see 150") is mounted near an area of interest (e.g. the area in which the smelt contacts the fluid) and slave or guard sensors (see 150, 150') surround the master sensor (see 150") and eliminate noise generated from outside the area of interest. For example, the acoustic emission sensor 150' having a waveguide 125 disposed in the fluid path of the disruptor 140, may continuously monitor the acoustic emissions 167 produced in the fluid path of the disruptor 140. The system may process the signal as described below and generate a signal profile indicative of normal disruptor operating conditions. A data processor 336 (FIG. 3) may then subtract the signal profile of the normal disruptor operating conditions from the signal recorded by the master sensor (see 150") positioned over the area in which the smelt contacts the green liquor 165. In this manner, one may use the master-slave technique to eliminate irrelevant background noise from the signal generated at the master sensor 150".

In other exemplary embodiments, the guard sensors (see 150, 150') may detect a baseline level of activity 442 (FIG. 4) representative of a first rate of smelt flow at normal operating conditions in a guard sensor's detection area. For example, the acoustic emission sensor 150' having a waveguide 125 disposed in the fluid path of the disruptor 140, may continuously monitor the acoustic emissions 167 produced in the fluid path of the disruptor 140. A data processor 336 communicating with the acoustic sensor 150' may register a first set of processed waveforms 432 (FIG. 4) indicative of a baseline level of activity 442 in the fluid path of the disruptor 140. Before a smelt influx occurs, the data processor 336 may further register a second set of processed waveforms 433 (FIG. 4) that exceeds the baseline level of activity 442 by more than 200%. The second set of processed waveforms 433 can be representative of a second rate of smelt flow. In certain exemplary embodiments, the data processor 336 may corroborate the first set of processed waveforms 432 produced from a guard sensor (see 150, 150') with a first set of processed waveforms 432 produced from a master sensor (see 150") to confirm that the dissolving tank 160 is operating at normal operating conditions. In still further exemplary embodiments, the data processor 336 may corroborate the second set of processed waveforms 433 produced by the guard sensors (see 150, 150') with the second set of processed waveforms produced by the master sensor (see 150"). By comparing the second sets of processed waveforms 433, the data processor may confirm the existence of a pre-influx fingerprint 372 (FIG. 3) and thereby initiate a response to prevent or contain the smelt influx.

Smelt droplets 130 may have an average temperature between 750° C. to 820° C. The average temperature of the green liquor 165 is about 70° C. to 100° C. To withstand the heat within the dissolving tank 160 and exposure to the fluid 145, the acoustic emission sensors 150 may have a housing 151 made of a material configured to withstand the high temperatures and pressures. Examples include aluminum, duplex stainless steel, or regular stainless steel. Furthermore, example acoustic emission sensors 150 having electronics or transducing elements disposed within the dissolving tank 160 may be configured to operate temperatures up to and above 100° C. or at temperatures up to and above 160° C. depending on the average temperature within the dissolving tank 160. Acoustic emission sensors 150 having electronics or transducing elements disposed outside of the dissolving tank may be configured to operate at temperatures up to and above 50° C.

Figure 3:
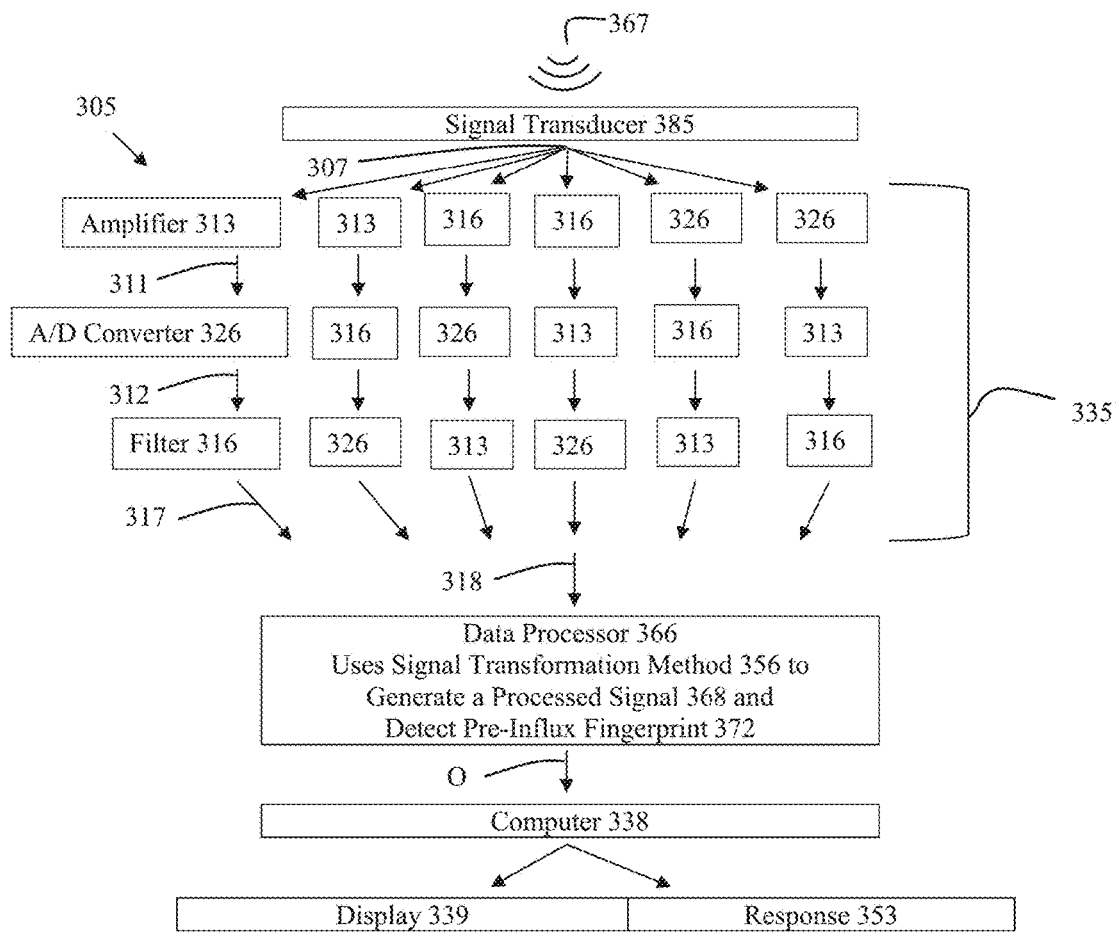
FIG. 3 is a flow chart depicting an exemplary embodiment of the acoustic emission system.
Figure 4:
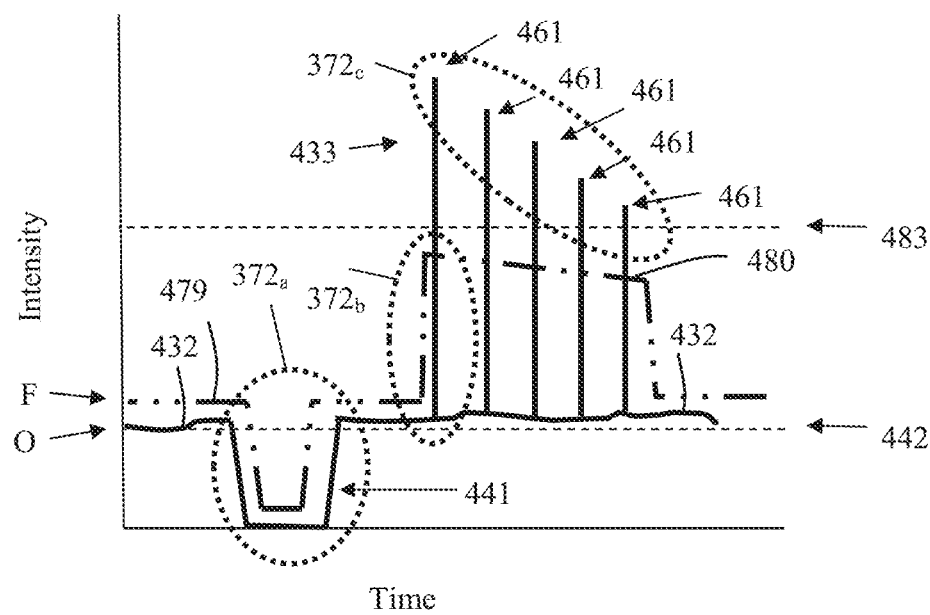
FIG. 4 is a graph schematically representing an exemplary pre-influx fingerprint.

Referring to FIGS. 1, 3, and 4, the acoustic emission sensor 150 detects acoustic emissions 167 continuously and the data processor 336 may continuously process or transform the digital signal in preparation for signal analysis (e.g. analyzing the processed signal to detect a pre-smelt influx fingerprint 372). In other exemplary systems, the acoustic emission sensor 150 may sample the acoustic emissions 167 at time intervals, such as, for example, at 10 milliseconds ("ms"), one second, or sixty seconds. Once processed, the data processor 336 outputs an output signal O. The output signal O may be transmitted to a computer 338 and a display 339. The output signal O comprises a first set of processed waveforms 432 representing a first rate of smelt flow (i.e. a baseline level of activity 442). Depending on the scale of the display 339, the first set of processed waveforms 432 may appear to have a substantially constant amplitude. On a display 339 (see FIG. 4, FIG. 5A, and FIG. 5B for display outputs), the first set of waveforms 432 having a substantially constant amplitude may appear to map to a substantially straight line representing the average amplitudes of the first set of waveforms 432. The display 339 may further output a floating threshold F, which is a threshold having an amplitude established by the time average measure of the signal. In FIG. 4, the floating threshold F represents the average amplitudes of the output signal O during a time interval. This first set of processed waveforms 432 represents a baseline level of activity 442 indicative of normal, even smelt flow and disruptor fluid flow based on inputs from one or more acoustic emission sensors 150. Normal even smelt flow may comprise a first rate of smelt flow. The baseline 442 may further indicate nominal recovery boiler activity. In other exemplary embodiments, acoustic emission sensors 150' placed near the outlet of each smelt spout 110 will detect the first signs of uneven smelt flows, problems with disruptors 140, and smelt influx.

Just before a sudden smelt influx, the amplitude of the processed signal 368 may be substantially lower than the baseline level of activity followed by a second set of processed waveforms 433 having amplitudes that are substantially higher than the baseline level of activity 442, such as 100% higher, more than 150% higher, at least 200%, more than 200% higher, at least 300%, more than 300% higher, at least 500%, or more than 500% higher than the baseline level of activity 442. The second set of processed waveforms 433 may be characterized by one or more amplitude peaks 461. The amplitude peaks 461 of the second set of processed waveforms 433 substantially exceed the average amplitudes of baseline level of activity 442 by at least 200%. The second set of processed waveforms 433 can represent a second rate of smelt flow. The pre-influx fingerprint 372 comprises the second set of waveforms 433 substantially exceeding the baseline level of activity 442 by at least 200%. In still other exemplary embodiments, one or more amplitudes peaks 461 in the second set of waveforms 433 may further comprise the pre-influx fingerprint 372. In still other exemplary embodiments, the pre-influx fingerprint 372 may comprise three or more amplitude peaks 461 in the second set of waveforms 433 substantially exceeding the baseline level of activity 442. In still other exemplary embodiments, the pre-influx fingerprint 372 may comprise at least five amplitude peaks 461 in the second set of waveforms 433 substantially exceeding the baseline level of activity 442.

In the conditions leading up to a smelt influx, the frequency of acoustic emissions 167 may be lower than the baseline level of activity 442 at one or more of the smelt spouts 110. That is, once pre-processed and processed, the output signal O may further comprise a third set of processed waveforms 441 having amplitudes below the average amplitudes of the baseline level of activity 442. In systems comprising a display 339 or user interface, the third set of processed waveforms 441 may not be depicted, or the third set of processed waveforms 441 may be represented as a gap in the first set of processed waveforms 432. The lower rate of acoustic emissions 167 would be independent of process conditions that would otherwise account for a lower rate of acoustic emissions 167. An exemplary system 305 may compare processed signals 368 derived from the acoustic emission sensor 150' disposed near the disruptor 140 and smelt spout 110 with processed signals 368 derived from the acoustic emission sensor 150 disposed throughout the dissolving tank 160 to determine whether a lower rate of acoustic emissions 167 is an expected outcome of current dissolving tank or recovery boiler conditions. If the lower rate of acoustic emissions 167 (and resulting third set of processed waveforms 441) is not an expected outcome of current dissolving tank or recovery boiler conditions, a low rate of acoustic emissions 167 can be indicative of smelt spout blockage, or indicate fluctuating smelt flow in the recovery boiler 100 and may further comprise the pre-influx fingerprint 372.

As seen in FIG. 4, the pre-influx fingerprint 372 may comprise an initial pre-influx fingerprint $372_a$ characterized by the third set of processed waveforms 441 having a lower rate of acoustic emissions 167 that is not an expected outcome of process conditions and an imminent pre-influx fingerprint $372_b$ characterized by a second set of processed waveforms 433 having one or more amplitude peaks 461 exceeding the first set of processed waveforms 432 by more than 200%. In certain exemplary systems, the data processor 336 may initiate a response, such as an alarm, or a change in process condition, or initiate smelt containment upon detection of the initial pre-influx fingerprint $372_a$. In other exemplary systems, the data processor 336 may trigger a first alarm in response to detecting an initial pre-influx fingerprint $372_a$.

In other exemplary embodiments, the display 339 may display a first floating threshold 479 defined by the average amplitudes of the first set of processed waveforms 432 and a second floating threshold 480 defined by the second set of processed waveforms 433. The pre-influx fingerprint 372 may further comprise a transition (see 372$_b$) from the first floating threshold 479 to the second floating threshold 480, wherein the second floating threshold 480 exceeds the first holding threshold 479 by at least 100%. That is, the pre-influx fingerprint 372 may comprise an increase in the floating threshold F by more than 100%.

It will be appreciated that transforming an acoustic emission signal with any signal processing formula to predict a smelt influx, wherein the signal is above 20 KHz, and emanates from banging in a dissolving tank is considered to be within the scope of this disclosure. The 20 KHz frequency represents the upper limit of human hearing. It will be further appreciated that transforming an acoustic emission signal with any signal processing formula to predict a smelt influx, wherein the signal is above 100 KHz, and emanates from banging in a dissolving tank is considered to be within the scope of this disclosure.

In other exemplary embodiments, the pre-influx fingerprint 372 may comprise an amplitude decay pre-influx fingerprint 372$_c$ in which two or more amplitude peaks 461 surpass the threshold 483 within a set unit of time. The threshold 483 may be a voltage threshold, floating threshold, system examination threshold, or other threshold set by the user or instrument against which the pre-influx fingerprint 372 may be compared. For example, when the display 339 displays an output signal O at a one second resolution, the amplitude decay pre-influx fingerprint 372$_c$ may comprise two or more amplitude peaks 461 surpassing the threshold 483 every second. In embodiments in which the display 339 displays an output signal O at 10 ms, the amplitude decay pre-influx fingerprint 372$_c$ may comprise two or more amplitude peaks 461 surpassing the threshold 483 every 10 milliseconds. The longer the amplitude peaks 461 surpass the threshold 483, the more likely the smelt influx will cause the dissolving tank to explode (see 531, FIG. 5B).

Figure 2:
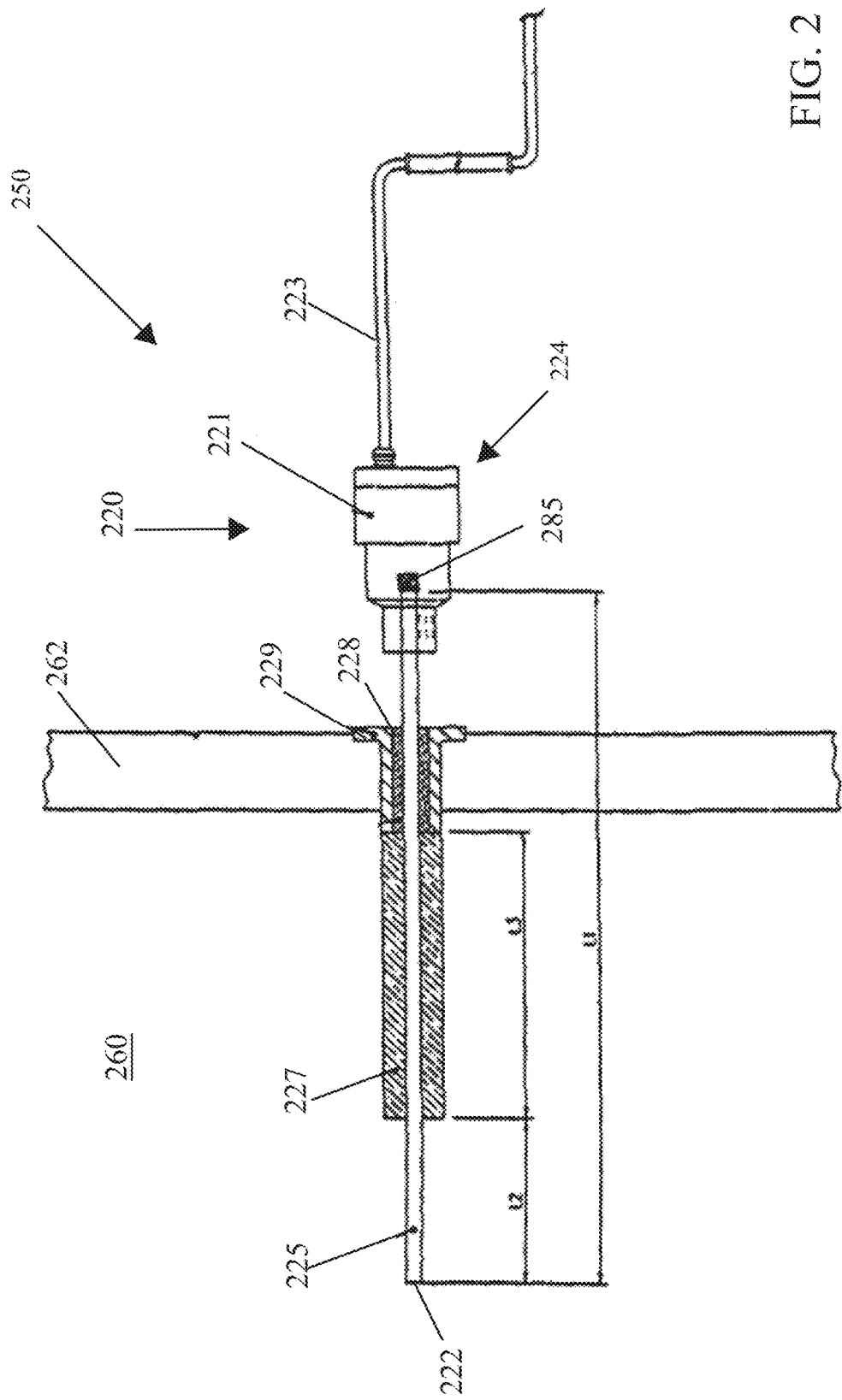
FIG. 2 is detailed cross sectional view of acoustic emission sensor.

FIG. 2 depicts acoustic emission sensor 250 wherein the acoustic waves 167 (FIG. 1) vibrate the wave guide 225. The acoustic emission sensors 250 are configured to detect acoustic emissions 167 continuously. The acoustic emission sensor 250 has a wave guide 225 engaged to a transducer 285. In the depicted embodiment, the transducer 285 is a piezoelectric crystal, although it will be understood that other transducer known in the art may be used. The wave guide 225 has a length L$_1$ extending from the transducer 285 to a reading end 222.

A protective sleeve 227 may shield a portion of the wave guide length L$_3$ from smelt splashes, liquor splashes, and the temperature and pressure inside the dissolving tank 260. An exposed portion of the wave guide L$_2$ may be directly exposed to the green liquor 165 within a dissolving tank 265. Operators may insert the wave guide 225 through an inlet sleeve 229 disposed within the wall 262 or top 164 of the dissolving tank 260. Insulation 228 may seal the opening in the inlet sleeve 229 and isolate the wave guide 225 from dissolving tank walls 262 and sleeve 229 to minimize background signals, not relevant to banging detection.

As shown in FIGS. 2 and 3, acoustic waves 167 contact the wave guide 225, the wave guide 225 vibrates and mechanically transfers the acoustic wave 167 to the transducer 285. The acoustic emission sensor 250 may have a threshold level. The threshold level is a threshold amplitude against which the amplitudes of the acoustic emissions 167 are compared. The acoustic emission sensor 250 may be configured to register acoustic emissions 167 that have amplitudes greater than the threshold level or less than the threshold level. The transducer 285 then transduces the acoustic emissions 167 above the threshold level into an initial electric signal 307. The transducer 285 and associated electronics are generally protected within a housing 220.

A pre-amplifier 221 can then amplify the signal 307. Subsequent amplifiers (see 313) may further amplify the signal 307 before the data processor 336 receives the pre-processed signal 318. A typical acoustic emission sensor 250 generally has a pre-installed preamplifier 221, although nothing in this disclosure limits the acoustic emission sensors 250 to having pre-installed preamplifiers 221. The preamplifier 221 may amplify the signal 307 by generally 40 to 60 decibels ("dB"). A filter 316, such as a high pass, low pass, or band pass filter may then filter the signal to a programmed frequency range above 20 KHz. In other exemplary embodiments, the filter 316 may filter the signal to a programmed frequency range of above 100 KHz. An A/D converter 326 may then convert the analog signal 307 to a digital signal 312. The data processor 366 receives the amplified and filtered digital signal 311, 317, 312 (i.e. the pre-processed signal 318) and performs a processing or signal transformation method 356 to generate a processed signal 368. The data processor 366 may further be configured to detect a pre-influx fingerprint 372. An acoustic emission sensor 250 may include electronics for complete signal processing, which may include an amplifier 313, filter 316, A/D converter 326, data processor 366, and display 339. In other exemplary embodiments in which the acoustic emission sensor 250 does not contain all processing elements, the cable 223 may transmit the signal to the next signal processor. In still other exemplary embodiments, the acoustic emission sensor 250 may transmit the signal wirelessly.

Although acoustic emission sensors 250 may be configured to detect a range of acoustic emissions, acoustic emission sensors 250 typically have a resonant frequency. That is, the acoustic emission sensor 250 is generally configured to provide a highly defined electric signal at the resonant frequency. While the acoustic emission sensor 250 may detect acoustic waves 167 and transmit signals 307 above or below the resonant frequency, the detail of these non-resonant signals is comparatively less than the detail detected at the resonant frequency. In piezoelectric sensors, the thickness of the piezoelectric crystal defines the resonant frequency of the sensor. In an exemplary embodiment, the acoustic emission sensor 250 may have a resonant frequency above 20 KHz and desirably above 100 KHz.

Piezoelectric sensors also typically have a temperature at which the piezoelectric crystal loses its piezoelectric properties. In embodiments where the acoustic emission sensor 250 is a piezoelectric sensor it is desirable to select a piezoelectric sensor configured to function at temperatures typical to dissolving tanks 260.

FIG. 3 is a flow chat representing an exemplary acoustic emission system 305 for detecting a pattern of banging in a dissolving tank 260. One or more acoustic emission sensors 250 detect acoustic emissions 367 continuously. The signal transducer 385 transduces the acoustic emissions 367 to an electric analog signal 307. Pre-processors 335 then pre-process the signal 307. The order in which the signal 307 undergoes pre-processing prior to the application of the signal transformation method 356 is immaterial. The pre-processors 335 may comprise a filter 316, an amplifier 313, an A/D Converter 326, or a computer 338. Signal pre-processing may comprise one or more pre-processors 335, less than all listed pre-processors 335, or multiple types of select pre-processors 335. For example, pre-processing may comprise both pre-amplifying the signal by 40 dB to 60 dB in the acoustic emission sensor 250 and further amplifying the signal in an amplifier disposed outside of the acoustic emission sensor 250; however, both the pre-amplifier disposed inside the acoustic emission sensor 250 and the amplifier disposed outside of the acoustic emission sensor 250 are considered amplifiers 313 for purposes of pre-processing and pre-processors 335.

The filter 316 generates a filtered signal 317. The filter 316 may be an analog filter, high pass filter, low pass filter, band pass filter, digital filter or other filter used in signal processing. The filter 316 filters out undesirable low frequencies (high pass filter), undesirable high frequencies (low pass filter), or both undesirable high frequencies and low frequencies (band pass filter). Operators may select the desired filter 316 manually. In the exemplary systems disclosed herein, operators may isolate signal frequencies between 100 KHz and 300 KHz. This range is sufficiently high to escape most mechanical noise, but is also low enough to detect acoustic emissions 167 sufficiently far from the source. This can allow the operators to place the acoustic emission sensors 150 in the dissolving tank walls 262 or proximate to the dissolving tank 260. In other exemplary embodiments, the filter 316 may be set automatically. Undesirable frequencies below 20 KHz (e.g. frequencies irrelevant to predicting sudden smelt influx) can be filtered out in this manner. In other exemplary embodiments, undesirable frequencies below 100 KHz may be filtered out in this manner.

Without being bounded by theory, a high pass filter may be desirable to filter out hydraulic noise, which may emanate from turbulent flow of fluids, boiling of fluids, and leaks. The high pass filter may further filter out mechanical noise emanating from mechanical parts in contact with the system. Cyclic noise, e.g. repetitive noise from reciprocating or rotary machinery, may also be filtered out with a high pass filter. A low pass filter may be useful for filtering out electro-magnetic noise. Applicant has discovered that the frequency of mechanical noise is usually lower than an acoustic emission burst from the highest frequency range of banging in the dissolving tank 260.

The amplifier 313 amplifies the amplitude of the signal to produce an amplified signal 311. An amplifier 313 may be an analog amplifier, pre-amplifier, digital amplifier, or other amplifier used in signal processing. An amplifier may pre-amplify the signal 307 produced from the signal transducer 385. The signal 307 may be further amplified after filtering and an A/D converter 326 may then convert the analog signal to a digital signal 312. Variations in the order of pre-processing are considered to be within the scope of this disclosure.

It will be understood that some or all of the pre-processors 335 may reside in the acoustic emission sensor 250, (e.g. within a single housing 251, on a single circuit board, etc.). In other exemplary embodiments pre-processors 335 may reside in the system as separate devices outside of the acoustic emission sensor 250.

The pre-processors 335 produce a pre-processed signal 318. A data processor 366 receives the pre-processed signal and applies a signal transformation method 356 to generate a processed signal 368. The processed signal 368 may be output from the data processor as the output signal O. The data processor 366 may be a field programmable gate array ("FGPA"). In still other exemplary embodiments, the data processor 366 may be an application-specific integrated circuit ("ASIC"). The data processor 366 receives the processed signal 318 and may perform continuous counting analysis as the signal transformation method 356.

In other exemplary embodiments, the data processor 366 may conduct a Fast Fourier Transform ("FFT") as the signal transformation method 356. In other exemplary systems, the signal transformation method 356 may comprise the root mean square ("RMS") method, standard deviation method, skewness method, kurtosis method, mean method, variance method, or the signal transformation method may use fuzzy logic, neural networks, and other signal processing methods to produce a processed signal 368. The data processor 366 may be further configured to detect a pre-influx fingerprint 372 before outputting an output signal O.

The output signal O may then be sent to a computer 338, which may be configured to confirm the pre-influx fingerprint 372 and display the output signal O on a display 339 or other user interface. By way of example, the output signal O may be displayed as a continuous frequency spectrum display, a long-time envelope, or by displaying merely portions of the signal that exceed predetermined thresholds (e.g. the portions that exceed the first set of processed waveforms 432).

In certain exemplary embodiments, the display 339 may display the processed signal in which the processed signal is a rectified, time averaged acoustic emission signal depicted on a linear scale and reported in volts. The display 339 may further display the energy of the processed signal, wherein the energy of the processed signal is evaluated as the integral of the volt-squared function over time. The signal strength may also be displayed in which the signal strength is measured as the areas of the rectified acoustic emission signal in units proportional to volt-seconds. In still other exemplary embodiments, the display 339 may display only processed signals that exceed a threshold.

The threshold may be user-adjustable, fixed, or a floating threshold. The floating threshold varies with time as a function of noise output. A floating threshold can be used to distinguish between background noise and acoustic emission events in conditions in which the background noise is high and varying. A voltage threshold is a voltage level on an electronic comparator such that signals with amplitudes larger than this level will be recognized.

The display 339 may display count trend resolutions at 10 milliseconds ("ms"), one second, 60 seconds, or any other time interval selected by the operators. All other trends (Fast Fournier Transform, root mean square, etc. are desirably displayed at a one second resolution. Because the acoustic emission sensors 150 detect acoustic emissions 167 continuously, the total time trend can last for as long as the acoustic emission sensors 150 remain functional, such as for a period of years.

In further exemplary embodiments, when the computer 338 recognizes the pre-influx fingerprint 372, the computer 338 may initiate a response 353. The response 353 may comprise changing a process condition, such as restricting or blocking smelt flow with a restrictor plate such as the one disclosed in U.S. Pat. No. 9,206,548. In other embodiments, the response 353 may comprise adjusting a process condition within the recovery boiler. Changing a process condition within the recovery boiler may include adjusting the combustion rate, rate of black liquor flow, rate of air flow, air flow path, black liquor flow path, temperature, pressure, and concentration of reactants. Changing process condition may include changing a second rate of smelt flow indicative of a smelt influx into a first rate of smelt flow indicative of a baseline level of activity 442, such as by restricting the rate of smelt flow in the smelt spout 110 or by preventing the smelt 115 in the smelt spout 110 from entering the dissolving tank 160. Software may be configured to initiate the response 353. In yet other embodiments, the response 353 may comprise, increasing the rate of fluid exiting the disruptor 140. In still other exemplary embodiments, the response 353 may comprise triggering one or more alarms. Combinations of the disclosed responses 353 and other common ways to control smelt flow are considered to be within the scope of this disclosure.

In certain exemplary embodiments, the data processor 366 may reside in the computer 338. In other exemplary embodiments, a data process disposed outside of the computer 338 may begin processing the pre-processed signal 318 such as by using a signal transformation method 356 to transform the signal and then transmit the transformed signal to the computer 338 for pre-influx fingerprint detection. In still other exemplary embodiments, a computer 338 may comprise a pre-processor 335 and perform some or all of the signal pre-processing. In still other exemplary embodiments, a computer 338 may apply a signal transformation method 356.

Figure 5A:
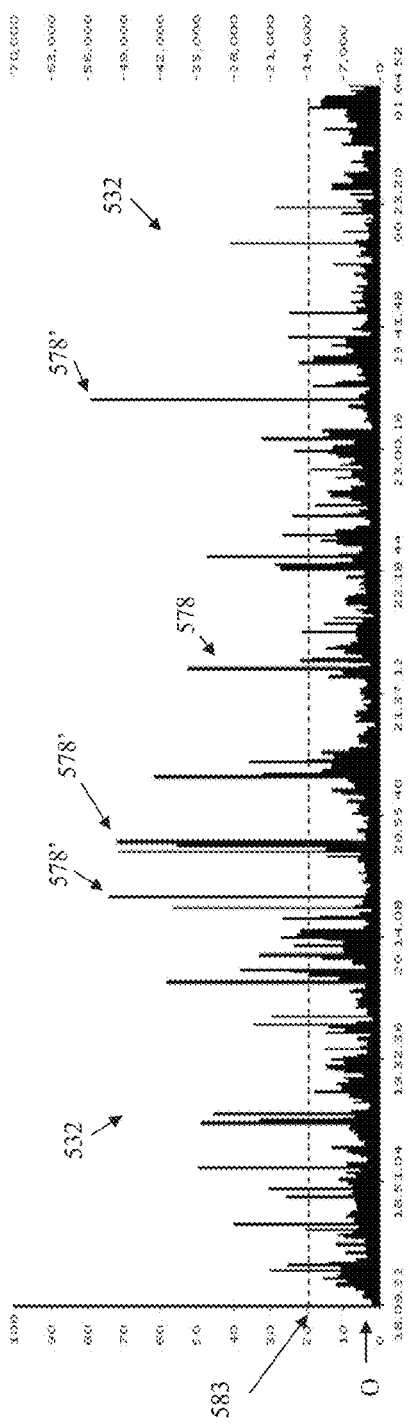
FIG. 5A is depicts an FFT output on a display, wherein the output is a first set of processed waveforms representing a baseline level of activity.

FIG. 5A depicts an FFT output signal O that may be seen on a display 339. The output signal O is a first set of processed waveforms 532 representing a baseline level of activity 442 (FIG. 4) in a dissolving tank 160. In the depicted embodiment the pre-processed signal 318 has been filtered to above 100 KHz. This is well beyond the range of human hearing and microphones that detect audio waves transmitted through air. A user may set a threshold 583 at for example, at 20. In the depicted scale, the first set of processed waveforms 532 has occasional, randomly distributed, threshold-surpassing peaks 578. The amount of times these occasional threshold-surpassing peaks 578' generally surpass the threshold 583 depends on where the threshold is set and the specified period of time. For example, when the display 339 is displaying an amplitude peak 578 every second, the occasional threshold-surpassing peaks 578' may not surpass the threshold 583 more than a few times per minute. In the depicted embodiment, the threshold 583 is set at 20 and the display resolution is set to one second. Generally, occasional threshold-surpassing peaks 578' do not surpass the threshold 583 at three consecutive seconds. Because the processed signal 368 (FIG. 3) is a signal above 20 KHZ and the background noise has been filtered out during pre-processing 335, the occasional threshold-surpassing peaks 578' represent normal smelt banging, or periodic minor smelt influxes that do not jeopardize the structural integrity of the dissolving tank. The first set of processed waveforms 532 and baseline level of activity 442 comprise these occasional threshold-surpassing peaks 578'. It will be understood that the occasional threshold-surpassing peak represent normal smelt banging activity. The depiction of these occasional threshold-surpassing peaks will vary depending on a specific dissolving tank environment and the rate and scale at which users choose to display the output O. The display 339 may further display a floating threshold F (FIG. 4), which represents the average amplitudes of the output signal O during a specified time interval.

Figure 5B:
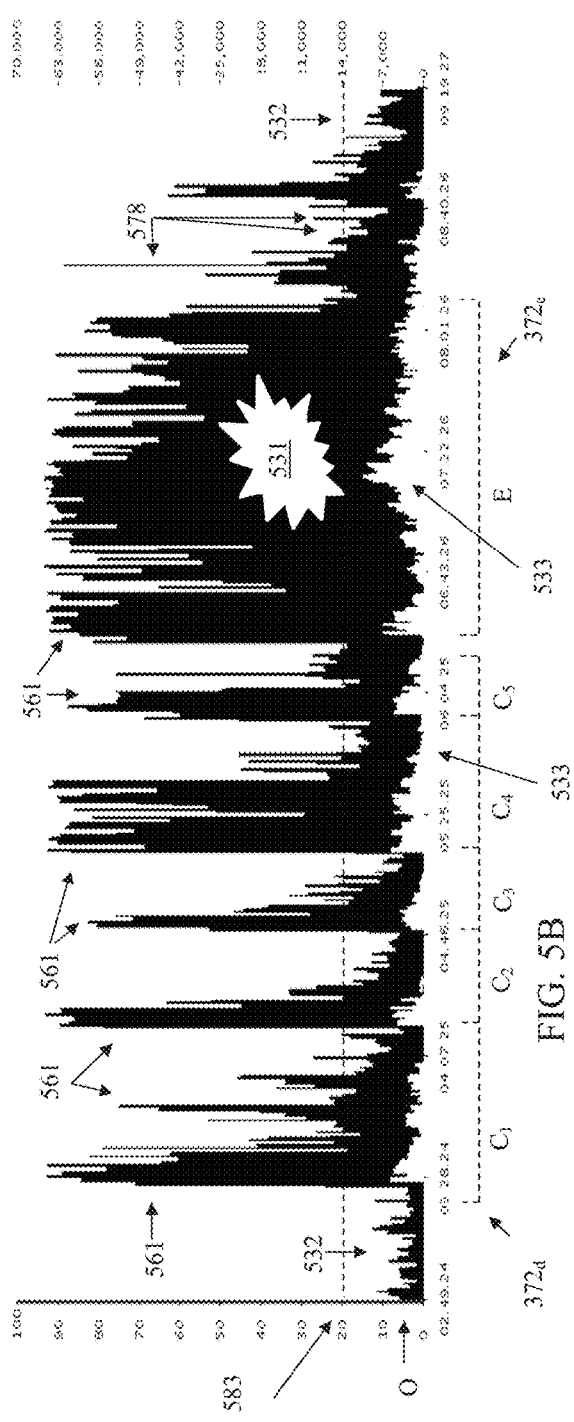
FIG. 5B depicts an FFT output on a display, wherein the output has a second set of processed waveforms exceeding the baseline by more than 200%.

In FIG. 5B, the FFT output signal O comprises a first set of processed waveforms 532 transitioning into a second set of processed waveforms 533. In the depicted embodiment the pre-processed signal 318 has been filtered to above 100 KHz. The second set of processed waveforms 533 comprises a pattern of amplitude peaks 561 that consistently surpass the threshold 583 over a specified period of time. For example, in FIG. 5B, the threshold 583 is set at 20 and the display 339 displays an amplitude peak every second.

The pre-influx-fingerprint 372 may comprise the pattern of amplitude peaks 561. Furthermore, the pre-influx fingerprint 372 may comprise a cyclic pre-influx fingerprint $372_d$ characterized by repeating amplitude decay pre-influx fingerprints (see $372_c$, FIG. 4) over a time interval. In the depicted embodiment, the cyclic pre-influx fingerprint $372_d$ comprises at least five amplitude decay pre-influx fingerprints $C_1$, $C_2$, $C_3$, $C_4$, and $C_5$. In the depicted embodiment, the cyclic pre-influx fingerprint $372_d$ occurred over a period of approximately three hours. It will be understood however, that a cyclic pre-influx fingerprint $372_d$ may comprise at least two amplitude decay pre-influx fingerprints $372_c$. The system described herein may initiate a change in process condition upon detection of any pre-influx fingerprint 372. In the depicted embodiment, the system may trigger a first alarm or change in process condition upon detection of the cyclic pre-influx fingerprint $372_d$ and a second alarm or change in process condition upon detection of a prolonged pre-influx fingerprint $372_e$.

The pre-influx fingerprint 372 may comprise a prolonged pre-influx fingerprint $372_e$. A prolonged pre-influx fingerprint $372_e$ is shown in FIG. 5B, over time interval E. A prolonged pre-influx fingerprint $372_e$ has multiple amplitude peaks 561 over the resolution interval and may not readily exhibit the amplitude decay pre-influx fingerprint $372_c$ or the cyclic pre-influx fingerprint $372_d$. It will be understood that the time interval E may vary depending upon the configurations and conditions of a particular dissolving tank 160 and the sampling frequency of the acoustic emission sensor 150, data processor 366 and resolution of the output signal O. In the depicted output signal O for example, the time interval E occurred over approximately one hour and forty five minutes. Regardless of how the prolonged pre-influx fingerprint $372_e$ is depicted or displayed, the prolonged pre-influx fingerprint $372_e$ indicates that a smelt influx is imminent or presently occurring. The system, or a computer in the system, may initiate an immediate change in process conditions or contain the smelt in response to detecting a prolonged pre-influx fingerprint $372_e$. If smelt flow is not contained upon detection of a prolonged pre-influx fingerprint $372_e$ an explosion 531 may be imminent. Upon adjustment of a process condition or containment of the smelt influx, the second set of processed waveforms 533 may transition back into the first set of processed waveforms 532 indicative of a baseline level of activity 442.

The pre-influx fingerprint 372 may further comprise a count trend and a Fast Fourier Transform trend, wherein the count trend depicts decreasing banging intensity in the dissolving tank 160 prior to frequency bands in the Fast Fourier Transform trend surpassing the first set of processed waveforms 432 by more than 300%.

Furthermore, an exemplary method of predicting a smelt influx in a dissolving tank may comprise: detecting acoustic emissions emanating from smelt banging within the dissolving tank with an acoustic sensor; converting the acoustic emissions into an initial electric signal; amplifying the initial electric signal to produce an amplified signal; filtering the amplified signal to a programmed frequency range of greater than 20 KHz; outputting a first output signal in the programmed frequency range, wherein the first output represents a baseline level of activity 442 within the dissolving tank in the absence of a smelt influx; outputting a second output signal substantially exceeding the first output signal by more than 200%, wherein the second output signal comprises signal peaks, and wherein three or more signal peaks in the second signal output comprise the pre-influx fingerprint; reducing smelt flow into the dissolving tank in response to the pre-influx fingerprint.

An exemplary system may comprise: a dissolving tank adjacent to a recovery boiler, wherein a smelt spout is in fluid communication with the recovery boiler and the dissolving tank; smelt disposed in the smelt spout, wherein the smelt flows from the recovery boiler through the smelt spout into the dissolving tank at a first rate, and wherein the smelt contacts a liquid in the dissolving tank and thereby generates acoustic emissions; an acoustic emission sensor having a reading end oriented to detect the acoustic emissions emanating from the dissolving tank, wherein the acoustic emission sensor has a transducer in signal communication with the reading end, and wherein the transducer is configured to transduce the acoustic emissions into an initial electric signal; a pre-processor configured amplify, filter, and digitize the initial electric signal to produce a pre-processed signal having a frequency of greater than 20 KHz, wherein the pre-processor is disposed downstream of the transducer; a data processor in signal communication with the pre-processor, wherein the data processor is configured to transform the pre-processed signal with a transformation method to produce an output signal, wherein the output signal comprises a first set of processed waveforms representative of the first rate, and a second set of waveforms representative of a second rate of smelt flow, the second set of processed waveforms having amplitude peaks exceeding the first set of processed waveforms by more than 200% to comprise a pre-influx fingerprint.

A further exemplary system may comprise: a dissolving tank adjacent to a recovery boiler, a smelt spout having a first end proximate a recovery boiler and a second end opposite the first end proximate a dissolving tank, wherein the smelt spout is configured to receive a smelt from the recovery boiler and convey the smelt to the dissolving tank; an acoustic emission sensor having a reading end configured to detect acoustic emissions emanating from the smelt contacting a liquid in the dissolving tank, and wherein the acoustic emission sensor has a transducer in signal communication with the reading end, and wherein the transducer is configured to transduce the acoustic emissions into an initial electric signal; a pre-processor configured amplify, filter, and digitize the initial electric signal to produce a pre-processed signal having a frequency of greater than 20 KHz, wherein the pre-processor is disposed downstream of the transducer; a data processor in signal communication with the pre-processor, wherein the data processor is configured to transform the pre-processed signal with a transformation method to produce an output signal, wherein the output signal comprises a first set of processed waveforms representative of a first rate of smelt flow, and a second set of waveforms representative of a second rate of smelt flow, the second set of processed waveforms having amplitude peaks exceeding the first set of processed waveforms by more than 200% to comprise a pre-influx fingerprint.

While this invention has been particularly shown and described with references to exemplary embodiments thereof, it will be understood by those skilled in the art that various changes in form and details may be made therein without departing from the scope of the invention encompassed by the appended claims.

What is claimed is:

1. A system comprising:
    a dissolving tank adjacent to a recovery boiler,
    a smelt spout having a first end proximate a recovery boiler and a second end opposite the first end, the second end being proximate a dissolving tank, wherein the smelt spout is configured to receive a smelt from the recovery boiler and convey the smelt to the dissolving tank;
    an acoustic emission sensor having a reading end configured to detect acoustic emissions emanating from the smelt contacting a liquid in the dissolving tank, and wherein the acoustic emission sensor has a transducer in signal communication with the reading end, and wherein the transducer is configured to transduce the acoustic emissions into an initial electric signal;
    a pre-processor configured to amplify, filter, and digitize the initial electric signal to produce a pre-processed signal having a frequency of greater than 20 KHz, wherein the pre-processor is disposed downstream of the transducer;
    a data processor in signal communication with the pre-processor, wherein the data processor is configured to transform the pre-processed signal with a transformation method to produce an output signal, wherein the output signal comprises a first set of processed waveforms representative of a first rate of smelt flow, and a second set of waveforms representative of a second rate of smelt flow, the second set of processed waveforms having amplitude peaks exceeding the first set of processed waveforms by more than 200% to comprise a pre-influx fingerprint.

2. The system of claim 1 further comprising the smelt disposed in the smelt spout.

3. The system of claim 1, wherein the acoustic emission sensor is disposed within the dissolving tank, within a wall of the dissolving tank, within a roof of the dissolving tank, within a base of the dissolving tank, or adjacent to the dissolving tank.

4. The system of claim 1, wherein the first end of the smelt spout is disposed in, engaged to, or extending toward the recovery boiler and the second end of the smelt spout is, disposed over, engaged to, or extending toward a dissolving tank.

5. The system of claim 1 further comprising a computer, wherein the computer is configured to detect the pre-influx fingerprint and restrict smelt flow into the dissolving tank after detecting the pre-influx fingerprint.

6. The system of claim 5, wherein the computer changes a process condition in response to detecting the pre-influx fingerprint.

7. The system of claim 5, wherein the pre-influx fingerprint further comprises a third set of processed waveforms having amplitudes below average amplitudes of the first set of processed waveforms, and wherein the computer initiates a response upon detection of the third set of processed waveforms.

8. The system of claim 1, wherein the data processor is an FPGA processor, wherein the FPGA processor transforms the pre-processed signal and continuously displays an intensity of chosen frequency bands in the second set of wave forms.

9. The system of claim 8, wherein the pre-influx fingerprint further comprises at least two amplitude peaks of the second set of waveforms exceeding the average amplitude of the first set of waveforms by at least 300% within a pre-defined time interval.

10. The system of claim 1, wherein the pre-processed signal has a frequency of greater than 100 KHz.

11. The system of claim 1, wherein the transformation method is selected from the group consisting of a continuous counting method, a Fast Fourier Transform, a root mean square method, a standard deviation method, a skewness method, a kurtosis method, a mean method, a variance method, a fuzzy logic method, and a neural network method.

12. The system of claim 1, wherein the acoustic emission sensor is selected from the group consisting of a piezoelectric sensor, an MEMS sensor or other acoustic emission sensor.

13. The system of claim 1, further comprising multiple acoustic emission sensors, and wherein each acoustic emission sensor further comprises a wave guide.

14. The system of claim 13, wherein the data processor transforms pre-processed signals produced by the multiple acoustic emission sensors.

15. The system of claim 13, wherein a wave guide extends into the liquid in the dissolving tank and a wave guide on a second acoustic sensor extends into a fluid emitted from the disruptor.

16. The system of claim 13, wherein an acoustic emission sensor of the multiple acoustic emission sensors extends through a wall of the dissolving tank or a top of the dissolving tank.

17. The system of claim 13, wherein an acoustic emission sensor of the multiple acoustic emission sensors is disposed proximate to the dissolving tank and outside of the dissolving tank.

18. The system of claim 1, wherein the first set of waveforms maps to a horizontal line representing the average amplitude of the first set of waveforms and wherein the horizontal line is a baseline level of activity.

19. The system of claim 1 further comprising a display, wherein the display displays the output signal as a continuous frequency spectrum display, a long-time envelope, or by displaying merely portions of the signal in the first set of processed waveforms.

20. The system of claim 1, wherein the pre-influx fingerprint further comprises a count trend and a Fast Fourier Transform trend, wherein the count trend depicts decreasing banging intensity in the dissolving tank prior to frequency bands in the Fast Fourier Transform trend surpassing the first set of processed waveforms by more than 300%.

21. The system of claim 5, wherein the pre-influx fingerprint further comprises a cyclic pre-influx fingerprint having repeating amplitude decay pre-influx fingerprints.

22. The system of claim 21, wherein the computer initiates a response after detecting the pre-influx fingerprint.

23. The system of claim 5, wherein the pre-influx fingerprint further comprises a prolonged pre-influx fingerprint and wherein the computer initiates a response after detecting the prolonged pre-influx fingerprint.

24. The system of claim 1, wherein the pre-influx fingerprint further comprises two or more amplitude peaks in the second set of processed waveforms surpassing a threshold within a pre-defined time interval.

25. The system of claim 1 further comprising a first floating threshold defined by the average amplitudes of the first set of processed waveforms and a second floating threshold defined by the second set of processed waveforms, wherein the pre-influx fingerprint further comprises a transition from the first floating threshold to the second floating threshold, wherein the second floating threshold exceeds the first holding threshold by at least 100%.

26. The system of claim 1, wherein the liquid in the dissolving tank is green liquor.

27. A method for predicting a smelt influx in a dissolving tank comprising:
    detecting acoustic emissions emanating from smelt banging in a dissolving tank with an acoustic emission sensor;
    generating an initial electric signal representing the acoustic emissions;
    amplifying the initial electric signal to produce an amplified signal;
    filtering the initial electric signal to a frequency range above 20 KHz to produce a filtered signal;
    converting the initial signal from an analog signal to produce a digital signal, wherein a pre-processed signal comprises the amplified signal, filtered signal, and digital signal;
    transforming the pre-processed signal with a data processor, wherein the data processor transforms the pre-processed signal with a transformation method, wherein the transformed pre-processed signal is an output signal;
    outputting the output signal, wherein the output signal comprises a first set of processed waveforms representing a first rate of smelt flow, and a second set of waveforms representing a second rate of smelt flow, the second set of processed waveforms have having amplitude peaks exceeding the first set of processed waveforms by more than 200%, and wherein the first set of processed waveforms and the second set of processed waveforms comprise a pre-influx fingerprint.

28. The method of claim 27 further comprising comparing multiple pre-processed signals in a programmed frequency range from multiple acoustic emission sensors.

29. The method of claim 27 further comprising transmitting the output signal to a computer and restricting smelt flow into the dissolving tank after a computer detects a pre-influx fingerprint.

30. The method of claim 27 further comprising transmitting the output signal to a computer and changing a process condition after the computer detects a pre-influx fingerprint.

31. The method of claim 30, wherein the pre-influx fingerprint further comprises a third set of processed waveforms having amplitudes below the average amplitudes of the first set of processed waveforms.

32. The method of claim 27, wherein the transformation method is selected from the group consisting of a continuous counting method, a Fast Fourier Transform, a root mean square method, a standard deviation method, a skewness method, a kurtosis method, a mean method, a variance method, a fuzzy logic method, and a neural network method.

* * * * *